(12) United States Patent
Taraphdar et al.

(10) Patent No.: US 10,513,477 B2
(45) Date of Patent: Dec. 24, 2019

(54) METHOD FOR IMPROVING PROPYLENE RECOVERY FROM FLUID CATALYTIC CRACKER UNIT

(71) Applicant: TECHNIP FRANCE, Courbevoie (FR)

(72) Inventors: Tanmay Taraphdar, Uttar Pradesh (IN); Babu N. Sharath, Uttar Pradesh (IN)

(73) Assignee: TECHNIP FRANCE, Courbevoie (FR)

(*) Notice: Subject to any disclaimer, the term of this patent is extended or adjusted under 35 U.S.C. 154(b) by 27 days.

(21) Appl. No.: 15/540,431

(22) PCT Filed: Dec. 29, 2015

(86) PCT No.: PCT/EP2015/081371
§ 371 (c)(1),
(2) Date: Jun. 28, 2017

(87) PCT Pub. No.: WO2016/107880
PCT Pub. Date: Jul. 7, 2016

(65) Prior Publication Data
US 2018/0002255 A1    Jan. 4, 2018

(30) Foreign Application Priority Data
Dec. 30, 2014    (EP) .................................... 14307211

(51) Int. Cl.
*B01D 5/00* (2006.01)
*C07C 7/04* (2006.01)
(Continued)

(52) U.S. Cl.
CPC ............ *C07C 7/005* (2013.01); *B01D 5/0075* (2013.01); *B01D 53/145* (2013.01); *C07C 7/04* (2013.01);
(Continued)

(58) Field of Classification Search
CPC .......................... B01D 5/0039; B01D 5/0075
See application file for complete search history.

(56) References Cited

U.S. PATENT DOCUMENTS 5,983,664 A    11/1999    Campbell et al.
6,271,433 B1    8/2001    Keady et al.
(Continued)

FOREIGN PATENT DOCUMENTS

FR    2817767    6/2002
WO    WO 2011/004123 A2    1/2011
(Continued)

OTHER PUBLICATIONS

PCT International Search Report dated Oct. 24, 2012 (Form PCT/USA/220) and PCT Opinion (Form PCT/ISA/237) (in French) corresponding to International Application No. PCT/EP2011/074051 filed Dec. 26, 2011 (in French).
(Continued)

*Primary Examiner* — Philip Y Louie
*Assistant Examiner* — Alyssa L Cepluch
(74) *Attorney, Agent, or Firm* — Locke Lord LLP; Peter J. Fallon; Joshua L. Jones

(57) ABSTRACT

The present invention relates to a method for treating a cracked stream stemming from a fluid catalytic cracker unit (FCCU) in order to improve propylene recovery. The present invention also relates to the corresponding installation to implement the method.

9 Claims, 1 Drawing Sheet

(51) Int. Cl.
  *C07C 7/11* (2006.01)
  *C07C 7/00* (2006.01)
  *C10G 70/04* (2006.01)
  *C10G 70/06* (2006.01)
  *C10G 7/02* (2006.01)
  *B01D 53/14* (2006.01)
  *C07C 7/09* (2006.01)

(52) U.S. Cl.
  CPC .................. *C07C 7/09* (2013.01); *C07C 7/11* (2013.01); *C10G 7/02* (2013.01); *C10G 70/043* (2013.01); *C10G 70/06* (2013.01); *C10G 2400/20* (2013.01); *C10G 2400/26* (2013.01); *C10G 2400/28* (2013.01)

(56) References Cited

U.S. PATENT DOCUMENTS

| | | | |
|---|---|---|---|
| 6,526,777 | B1 | 3/2003 | Campbell et al. |
| 2002/0007101 | A1 | 1/2002 | Senetar et al. |
| 2004/0177646 | A1 | 9/2004 | Wilkinson et al. |
| 2006/0004242 | A1 | 1/2006 | Verma et al. |
| 2007/0199865 | A1 | 8/2007 | Pham Duc |
| 2008/0081938 | A1 | 4/2008 | Schultz et al. |
| 2009/0194461 | A1 | 8/2009 | Bras et al. |
| 2009/0282865 | A1 | 11/2009 | Martinez et al. |
| 2010/0043488 | A1 | 2/2010 | Mak et al. |
| 2010/0263407 | A1 | 10/2010 | Paradowski et al. |
| 2011/0005273 | A1 | 1/2011 | Gahier et al. |
| 2011/0108457 | A1* | 5/2011 | Da Silva Ferreira Alves ............. C10G 7/00 208/70 |
| 2012/0172649 | A1 | 7/2012 | Yadav et al. |
| 2016/0083660 | A1* | 3/2016 | Fei .......................... C10G 55/06 585/653 |
| 2016/0130512 | A1* | 5/2016 | Hoehn ................... C10G 53/08 208/97 |

FOREIGN PATENT DOCUMENTS

| | | |
|---|---|---|
| WO | WO 2011/051614 A2 | 5/2011 |
| WO | WO 2011/056712 A3 | 5/2011 |
| WO | WO 2012/089709 A2 | 7/2012 |

OTHER PUBLICATIONS

Joe T. Lynch et al., "Texas plant retrofit improves throughput, C2 recovery," Oil & Gas Journal (Jun. 3, 1996), pp. 41-48.
Search Report dated Mar. 12, 2014 corresponding to French Application No. 13 56061.
Search Report dated Jun. 12, 2014 (in French).
EP Search Report dated Jul. 20, 2015—EP Application No. 14307211.4-1361.
PCT Notification of Transmittal of the International Search Report and the Written Opinion of the International Searching Authority, or the Declaration dated Apr. 8, 2016 for International Application No. PCT/EP2015/081371 filed Dec. 29, 2015.

* cited by examiner

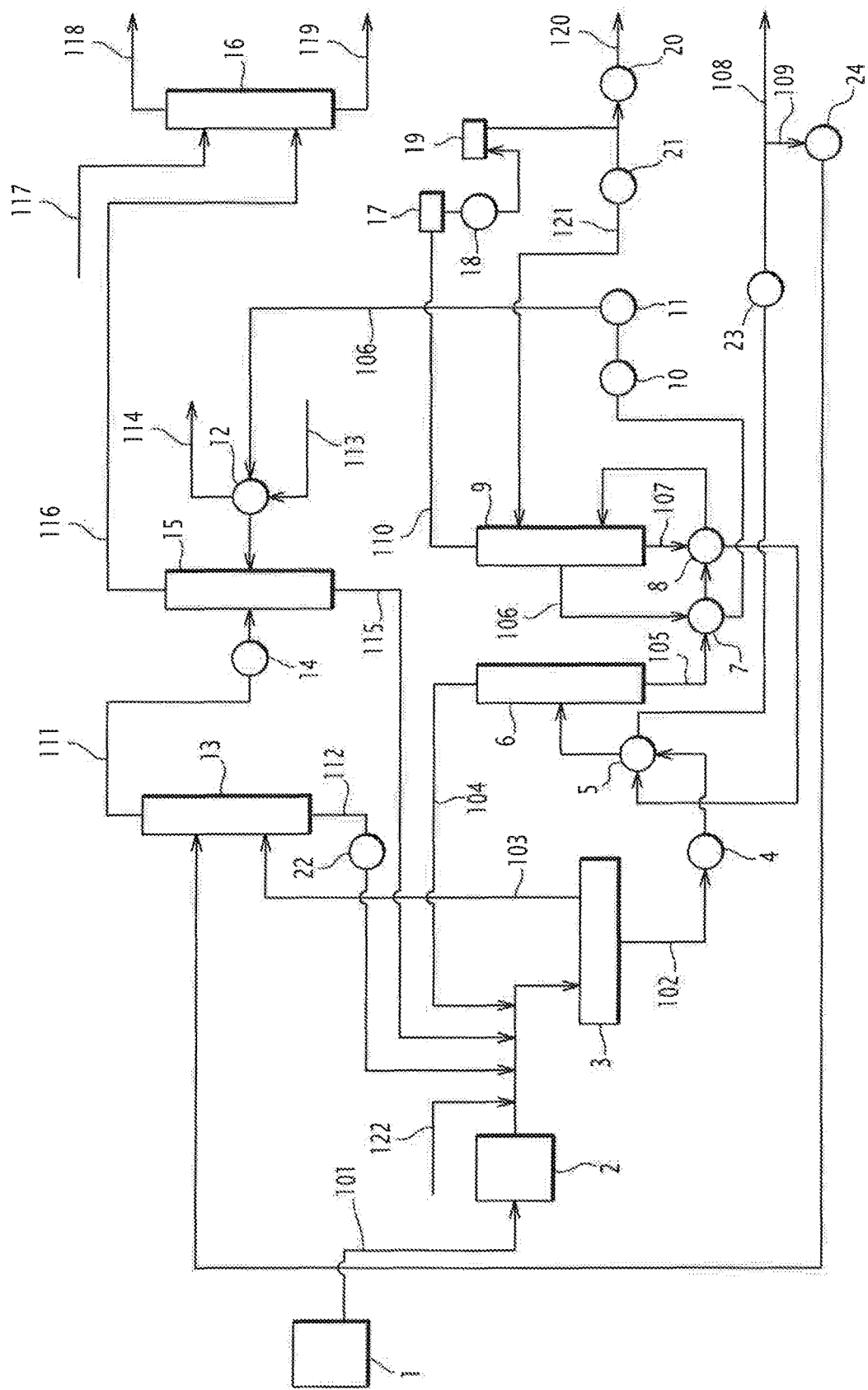

METHOD FOR IMPROVING PROPYLENE RECOVERY FROM FLUID CATALYTIC CRACKER UNIT

This application is a National Stage application of International Patent Application Number, PCT/EP2015/081371, filed on Dec. 29, 2015, which claims priority to EP 14307211.4, filed Dec. 30, 2014, the entire contents of which are incorporated herein by reference.

The present invention relates to a method for treating a cracked gas stream from a fluid catalytic cracker unit (FCCU) and more particularly to a method for improving propylene recovery from gas stream from a fluid catalytic cracker unit.

Propylene is a raw material for a wide variety of products. Propylene is principally used as monomer for the production of polypropylene. There is thus a strong market demand for propylene.

Fluid Catalytic Cracker Unit (FCCU) produces propylene as one of the products. The unsaturated gas plant downstream of the FCCU recovers propylene as part of Liquefied Petroleum Gas (LPG). Process schemes for propylene recovery from FCC off gases already exist with certain recovery of propylene potential. The typical recovery of propylene from unsaturated gas plant is around 94%. However, there is a considerable loss of propylene in fuel gas with the existing conventional schemes. Although fuel gas can be reused in the installation, an increase in propylene recovery would be more valuable for the operator of the installation.

There is thus a need to improve propylene recovery rate from stream from fluid catalytic cracker unit.

An object of the invention is therefore to provide a method for improving propylene recovery from streams from fluid catalytic cracker unit, for example in a range of 2 to 3 wt % of propylene potential compared to conventional methods.

Another object of the invention is also to provide an installation in order to implement this method.

For this purpose, the subject matter of the invention is a method for treating a cracked streams (gas stream and liquid stream) stemming from a fluid catalytic cracker unit (FCCU) comprising the following steps:

compressing and partly condensing the gas stream from the main fractionator column overhead receiver of the FCCU;
separating the partly condensed gas stream in order to recover an upstream liquid and an upstream gas;
heating the upstream liquid;
introducing this heated liquid into an upstream stripper for recovering at the top of the stripper a stream rich in C2 compounds and at the bottom a first liquid stream rich in C3+ hydrocarbons;
introducing the first liquid stream rich in C3+ into a first heat exchanger;
introducing the liquid recovered from the first heat exchanger into a stabilizer column for recovering at the top of the stabilizer column a stream rich in C3 and C4 hydrocarbons and from the side of the stabilizer column a liquid stream rich in C5 and C6, and from the bottom of the stabilizer column a liquid stream rich in C5, C6 and C7+ hydrocarbons;
introducing the liquid stream rich in C5 and C6 into the first heat exchanger;
introducing the liquid stream rich in C5, C6 and C7+ hydrocarbons from bottom of the stabilizer column into a primary absorber and introducing the upstream gas into a primary absorber for recovering at the top of the primary absorber a first gas stream; and at the bottom of the primary absorber a second liquid stream;
introducing lean oil into a sponge absorber;
cooling the first gas stream from primary absorber and introducing it into a propylene absorber;
cooling the liquid stream rich in C5 and C6 hydrocarbons from the first heat exchanger;
introducing the liquid stream rich in C5 and C6 recovered from the first heat exchanger into the propylene absorber;
recovering a bottom liquid rich in C3 hydrocarbons at the bottom of the propylene absorber and a top gas poor in C3 hydrocarbons at the top of the propylene absorber;
introducing the top gas recovered at the top of the propylene absorber into the sponge absorber, preferably to recover a fuel gas and a rich oil.

The stream rich in C5 and C6 is also poor in C7+ hydrocarbons.

Advantageously, the inventors have discovered that the stream rich in C5 and C6 hydrocarbons and poor in C7+ hydrocarbons has a good affinity to absorb propylene from light off gases. It thus enables to increase propylene recovery in the propylene absorber column.

Advantageously, the inventors have discovered that lowering the temperature of stream rich in C5 and C6 hydrocarbons enhances the capability of the stream to absorb more propylene from light off gases. It thus enables to increase propylene recovery in the propylene absorber column. Especially, the temperature of stream rich in C5 and C6 hydrocarbons sent into propylene absorber is comprised between 20 and 40° C., preferably between 28 and 32° C.

Advantageously, the inventors have discovered that lowering the temperature of gas stream recovered from top of the primary absorber before introducing it into propylene absorber enhances propylene absorption. It thus enables to increase propylene recovery in the propylene absorber column. Especially, the temperature of the gas stream recovered from top of the primary absorber before introducing it into propylene absorber enhances propylene absorption is at a temperature lower than or equal to 40° C., preferably between 25 and 40° C., more preferably between 38 and 40° C.

The method according to the invention can comprise a further step of mixing the liquid rich in C3 hydrocarbons, especially propylene, from the propylene absorber column with the stream resulted from the compression and partial condensation of the gas stream from the main fractionator before the separation of the resulting stream into the upstream liquid and the upstream gas. This further step enables to improve the recovering of C3 hydrocarbons, and especially propylene, compared to conventional scheme.

The method of the invention may further comprise one or more of the following features, taken individually or according to all technically possible combination(s):

the method comprises the step of introducing the liquid rich in C5 and C6 hydrocarbons recovered from the first heat exchanger into a second heat exchanger to cool with water and then into a third exchanger before its introduction into the propylene absorber, advantageously cooling with a cold propylene stream from a propylene recovery unit;
the method comprises the following steps of:
introducing the stream rich in C3 and C4 hydrocarbons from the top of the stabilizer into a condenser;
cooling the stream retrieved from this condenser;

separating the obtained stream into a liquid stream which is introduced into the stabilizer column as reflux and into a liquid stream sent to a LPG (Liquefied Petroleum Gas) treating unit to recover LPG;

the stream rich in C2 is mixed with the stream resulted from the compression and partial condensation of the gas stream from the main fractionator before the separation of the resulting stream into the upstream liquid and the upstream gas;

the second liquid fraction recovered at the bottom of the primary absorber is mixed with the stream resulted from the compression and partial condensation of the gas stream from the main fractionator before the separation of the resulting stream into the upstream liquid and the upstream gas;

Advantageously, the first gas stream is cooled before being introduced into the propylene absorber, this enables shifting thermodynamic equilibrium in favor of more propylene absorption into the liquid phase. Advantageously, the temperature of the first gas stream before introduction into the propylene absorber is between 35 and 50° C., preferably between 38 and 43° C., more preferably between 38 and 40° C.

Advantageously, the sponge absorber enables to capture gasoline range material, principally C5 compounds, which can be lost in the gases coming from the primary absorber. The resulting stream is a rich oil which can be sent to main fractionator column.

Advantageously, the liquid stream rich in C5, C6 and C7+ hydrocarbons recovered from the stabilizer column bottom can be separated in two liquid stream, a stabilized gasoline which can be stored and a recycle gasoline which can be sent to the primary absorber.

The implementation of this method enables an improvement of the propylene recovery from gas stream from fluid catalytic cracker unit in a range of 2 to 3 wt % compared to the conventional method.

The subject matter of the invention is further an installation for treating a cracked stream stemming (gas stream and liquid stream) from a fluid catalytic cracker unit (FCCU), of the type comprising:

means for compressing and partly condensing a gas stream from the main fractionator column overhead receiver of the FCCU;

means for separating the partly condensed gas stream to recover an upstream liquid and an upstream gas;

means for heating the upstream liquid;

a stripper column and means for introducing the heated upstream liquid into the stripper column in order to recover at the top of the stripper a stream rich in C2 compounds and at the bottom of the stripper a first liquid stream rich in C3+ hydrocarbons;

a first heat exchanger and means for introducing into this first heat exchanger the first liquid stream rich in C3+ hydrocarbons;

a stabilizer column and means for introducing the liquid stream rich in C3+ hydrocarbons from the first heat exchanger into the stabilizer column to recover from the side of the stabilizer column a first liquid stream rich in C5 and C6 hydrocarbons, at the bottom of the stabilizer column a second liquid stream rich in C5, C6 and C7+ hydrocarbons and at the top of the stabilizer column a gas stream rich in C3 and C4 hydrocarbons;

means for introducing the first liquid stream rich in C5 and C6 hydrocarbons into the first heat exchanger;

means for cooling the liquid stream rich in C5 and C6 hydrocarbons from the first heat exchanger;

a primary absorber and means for introducing to said primary absorber a liquid stream rich in C5, C6 and C7+ hydrocarbons from stabilizer column and the upstream gas from the separator for recovering at the top of the primary absorber a first gas stream and at the bottom of the primary absorber a liquid stream;

a propylene absorber and means for introducing to this propylene absorber the cooled liquid stream rich in C5 and C6 hydrocarbons;

a sponge absorber and means for introducing to this sponge absorber a lean oil;

means for cooling the first gas stream from the primary absorber;

means for introducing into the propylene absorber the first gas stream from the primary absorber for recovering at the top of the propylene absorber a gas stream poor in C3 hydrocarbons and at the bottom of the propylene absorber a liquid stream rich in C3 hydrocarbons;

means for introducing into the sponge absorber the gas stream poor in C3 hydrocarbons recovered at the top of the propylene absorber, preferably for recovering at the top of the sponge absorber a fuel gas and at the bottom a rich oil.

The installation may further comprise means for recycling and mixing the liquid stream rich in C3 hydrocarbons from the propylene absorber with the stream resulting from the compression and partial condensation of the gas stream from the main fractionator before the separation of the resulting stream into the upstream liquid and the upstream gas.

The installation of the invention may further comprise one or more of the following features, taken individually or according to all technically possible combination(s):

a second heat exchanger and means for introducing into said second heat exchanger the liquid stream rich in C5 and C6 hydrocarbons recovered from the first heat exchanger a third heat exchanger and means for introducing into said third heat exchanger the liquid stream rich in C5 and C6 hydrocarbons recovered from the second heat exchanger and advantageously a cold propylene stream preferably from a propylene recovery unit;

a fourth heat exchanger and means for introducing into this fourth heat exchanger the liquid rich in C5, C6 and C7+ and the liquid stream rich in C3+ hydrocarbons recovered from the first heat exchanger before introduction of the resulting stream rich in C3+ hydrocarbons into the stabilizer column;

a treatment unit of the liquid stream rich in C3 and C4 hydrocarbons from the stabilizer column comprising:
  a condenser and means for introducing into this condenser the liquid stream rich in C3 and C4 hydrocarbons from the top of the stabilizer;
  a heat exchanger and means for introducing into this heat exchanger the stream retrieved from the condenser;
  separation means for separating the obtained stream into a liquid stream which is introduced into the stabilizer column and a liquid stream sent to a LPG treating unit to recover LPG;

means for recycling and mixing the stream rich in C2 compounds with the stream resulting from the compression and partial condensation of the gas stream from the main fractionator before the separation of the resulting stream into the upstream liquid and the upstream gas;

means for recycling and mixing the liquid stream from the primary absorber with the stream resulting from the compression and partial condensation of the gas stream from the main fractionator before the separation of the resulting stream into the upstream liquid and the upstream gas.

The pressures given in the application are in barg which corresponds to the relative internal pressure measured with measuring gauge.

$P$ in barg (or relative pressure)=$P$ absolute in bar–$P$ atmospheric in bar

The process and installation of the invention may further be defined by the following preferred features, taken individually or according to all technically possible combination:

- the gas stream from the main fractionator column overhead receiver of FCCU is preferably at a temperature between 30 and 50° C., preferably between 38 and 43° C.;
- the gas stream from the main fractionator column overhead receiver of FCCU is preferably at a pressure comprised between 1 and 2 barg;
- the molar content of propylene in the gas stream from the main fractionator column overhead receiver of FCCU is preferably comprised between 15 and 50 mol %, preferably between 25 and 45 mol %;
- the stream from the compressor/condenser is at a pressure comprised between 14 and 16 barg;
- the liquid molar ratio of the stream from the compressor/condenser is higher than 70 mol %, preferably comprised between 70 and 80 mol %;
- the heated stream introduced into the stripper is at a temperature between 50 and 70° C., preferably between 55 and 65° C.;
- the stripper preferably operates at a pressure comprised between 14 and 17 barg, preferably between 15 and 16 barg;
- the molar content of C3+ hydrocarbons in stream rich in C2 hydrocarbon from the top of the stripper is lower than 45 mol %;
- the molar content of C1 and C2 hydrocarbons in stream rich in C2 hydrocarbon from the top of the stripper is comprised between 20 and 50 mol %, preferably between 30 and 40 mol %;
- the stream rich in C2 hydrocarbon from the top of the stripper is at a temperature between 50 and 70° C., preferably between 60 and 65° C.;
- the stream rich in C3+ hydrocarbons from the bottom of the stripper is at a temperature between 85 and 110° C., preferably between 95 and 100° C.;
- the molar content of C3+ hydrocarbons from the stream rich in C3+ hydrocarbons from the bottom of the stripper is higher than 95 mol %, preferably higher than 99 mol %;
- the stream rich in C3+ hydrocarbons from the bottom of the stripper after the first and second heat exchangers is at a temperature higher than 105° C.;
- the stabilizer column generally operates at a pressure comprised between 10.5 and 12.5 barg, preferably between 11 and 12 barg;
- the molar content of C5 and C6 hydrocarbons from the stabilizer is higher than 93 mol %;
- the molar content of C7+ hydrocarbons from the stabilizer side stream is lower than 22 mol %;
- the molar content of C5+ hydrocarbons in the stream rich in C3 and C4 hydrocarbons from the top of the stabilizer is lower than 1 mol %;
- the molar content of C3 and C4 hydrocarbons in the stream rich in C3 and C4 hydrocarbons from the top of the stabilizer is higher than 98 mol %;
- the stream rich in C5 and C6 hydrocarbons is cooled in the second heat exchanger at a temperature lower than 50° C., preferably lower than 42° C.;
- the stream rich in C5 and C6 hydrocarbons is cooled in the third heat exchanger at a temperature between 20 and 40° C., preferably between 28 and 32° C.;
- the hot stream of propylene is generally at a temperature between 25 and 35° C., preferably between 28 and 30° C.;
- the gas stream from the primary absorber is cooled at a temperature lower than 40° C.;
- the propylene absorber generally operates at a pressure between 12.5 and 14 barg; preferably between 12.9 and 13.5 barg;
- the molar content of C3 and C4 hydrocarbons in stream from the bottom of the propylene absorber is generaly greater than 10 mol %, preferably greater than 13 mol %;
- the molar content of C3 hydrocarbons in stream from the top of the propylene absorber is lower than 10 mol %, preferably lower than 7 mol %;
- the sponge absorber generally operates at a pressure between 12.5 and 14 barg, preferably between 13 and 13.6 barg;
- the C3 and C4 molar content of the stream from the top of stabilizer is higher than 98 mol %.

BRIEF DESCRIPTION OF THE DRAWING

The FIGURE is the functional block diagram of the installation according to the invention which is intended for applying the method according to the invention.

DETAILED DESCRIPTION

The invention will be better understood upon reading the description which follows, only given as an example and made with reference to the appended drawing.

In all of the following, a same reference designates a stream flowing in a conduit and the conduit which conveys this stream. Moreover, unless indicated otherwise, the pressures are meant to be in relative bars.

The installation according to the invention is illustrated in FIGURE. This installation comprises a compressor/condenser 2, a separator 3, a stripper 6 for producing a stream rich in C2 compound 104 and a stream rich in C3+ hydrocarbons 105. The installation further comprises a stabilizer column 9 to produce a stream 110 rich in C3 and C4 hydrocarbons, a side stream 106 rich in C5 and C6 compounds and a bottom stream 107 rich in C5, C6 and C7+ compounds. The installation also comprises a primary absorber 13 and a propylene absorber 15 which enables to recover a liquid stream 115 rich in C3 hydrocarbons, especially propylene. A sponge absorber 16 enables to absorb in a lean oil 117 gasoline range material (C5+ compounds) to produce a rich oil 119 and a fuel gas 118. The installation optionally comprises a treatment unit of the stream 110 rich in C3 and C4 hydrocarbons. This unit comprises a condenser 17 and a stabilizer receiver 19 to produce LPG 120 comprising of C3 and C4 hydrocarbons and a stream 121 as a reflux to stabilizer column (9) comprising C3 and C4 hydrocarbons.

In this installation, the propylene absorber 15 is in between the primary absorber 13 and the sponge absorber 16. The method according to the invention starts by providing a gas stream 101 having wide range of hydrocarbons from C1 to C7+ with impurities like nitrogen, $CO_2$, $H_2S$, water vapour etc. from the main fractionator column overhead receiver of an FCCU 1. The gas stream 101 has generally a temperature comprised between 30 and 50° C., preferably between 38 and 43° C., and a pressure generally comprised between 0.5 and 2.5 barg, especially between 1.0 and 2.0 barg. Its molar content in propylene is generally comprised between 15 and 50 mol %, preferably between 25 and 45 mol %. The gas stream 101 is compressed and partially condensed into a compressor/condenser 2. The pressure of the compressed gas stream is for example comprised between 14 barg and 16 barg and the liquid molar content is higher than 70 mol %, preferably comprised between 70 and 80 mol %. The resulting stream is introduced into a separator 3 which enables to recover an upstream liquid 102 and an upstream gas 103. The separator 3 is preferably a high pressure receiver, operating for example at a pressure higher than 14 barg. The upstream liquid 102 is pumped, thanks to a pump 4, and heated into a heat exchanger 5, advantageously with stabilizer column bottom stream 107. The resulting heated stream, preferably at a temperature comprised between 50 and 70° C., preferably between 55 and 65° C., is introduced into an upstream stripper 6 for recovering at the top of the stripper a stream 104 rich in C2 compounds and at the bottom of the stripper a liquid stream 105 rich in C3+ hydrocarbons. The stripper 6 generally operates at a pressure comprised between 14 and 17 barg, preferably between 15 and 16 barg. The molar content of C3+ hydrocarbons in stream 104 is generally lower than 45 mol %. The molar content of Cl, C2 hydrocarbons in stream 104 is for example comprised between 20 and 50 mol %, preferably between 30 and 40 mol %. The stream 104 is generally at a temperature comprised between 50 and 70° C., preferably between 60 and 65° C. The stream 105 is generally at a temperature comprised between 85 and 110° C., preferably between 95 and 100° C. The molar content of C3+ hydrocarbons in stream 105 is generally higher than 95 mol %, preferably higher than 99 mol %. The stream 104, rich in C2 compounds, is optionally recycled and mixed with the stream from the compressor/condenser 2. The liquid stream 105 rich in C3+ hydrocarbon is introduced into a first heat exchanger 7 and optionally into a second heat exchanger 8 to be heated at a temperature more than 105° C., the resulting stream is introduced into an upstream stabilizer column 9 for recovering a side liquid stream 106 rich in C5 and C6 hydrocarbons and a second bottom liquid stream 108 rich in C5, C6 and C7+ hydrocarbons and a gas stream 110 rich in C3 and C4 hydrocarbons. The stabilizer column generally operates at a pressure comprised between 10.5 and 12.5 barg, preferably between 11 and 12 barg. The molar content of C3 hydrocarbons in stream 106 and in stream 107 is practically nil (lower than 10 ppm). The molar content of C5 and C6 hydrocarbons in stream 106 is generally higher than 93 mol %. The molar content of C7+ hydrocarbons in stream 106 is generally lower than 22 mol %©. The molar content of C5 and C6 hydrocarbons in stream 110 is generally lower than 1 mol %. The molar content of C3 and C4 hydrocarbons in stream 110 is generally higher than 98 mol %. The liquid stream 107 is introduced into the second heat exchanger 8 to be cooled at a temperature comprised between 90 and 120° C., preferably between 100 and 110° C., and the resulting stream can be separated into two streams—a stabilized gasoline stream 108 for storage and a recycle gasoline stream 109 which can be introduced for example into the primary absorber 13.

Stream 107 can also be used in heat exchanger 5 to heat stream 102. Stream 106 is introduced into the first heat exchanger 7 and the resulting stream is introduced into a cooler 10 thanks to a pump 11 and the resulting cooled stream 106 at a temperature lower than 50° C., preferably lower than 42° C., is introduced into a heat exchanger 12 to be cooled at a temperature comprised between 20 and 40° C., preferably between 28 and 32° C., with a stream of cold propylene 113, preferably from a propylene recovering unit (PRU). A cooled stream 106 is recovered; this stream has generally at a temperature lower than 40° C., preferably lower than 31° C. Stream 106 is introduced into a propylene absorber 15 and a hot stream of propylene 114, generally at a temperature between 20 and 35° C., preferably between 28 and 30° C., which can be sent back to a propylene recovery unit. Recycle Gasoline stream 109 from the stabilizer column bottom is introduced into a primary absorber 13 for recovering a first gas stream 111 and a liquid stream 112 which can be recycled, thanks to a pump 22, and mixed with the stream 101 from the compressor/condenser 2. The gas stream 111 is preferably cooled to a temperature advantageously lower than 40° C. in a heat exchanger 14, preferably with water, before being introduced into the bottom of propylene absorber 15 for recovering at the bottom a liquid fraction 115 rich in C3 hydrocarbons which is preferably recycled and mixed with the stream 101 from the compressor/condenser 2, and at the top a gas stream 116. The propylene absorber generally operates at a pressure comprised between 12.5 and 14 barg, preferably between 12.9 and 13.5 barg. The molar content of C3 and C4 hydrocarbons in stream 115 is generally greater than 10 mol %, preferably greater than 13 mol %. The molar content of C3 hydrocarbon in stream 116 is generally lower than 10 mol %, preferably lower than 7 mol %. The gas stream 116 is then introduced into a sponge absorber 16, which generally operates at a pressure comprised between 12.5 and 14 barg, preferably between 13 and 13.6 barg, a lean oil is also introduced into the sponge absorber 16 for recovering a fuel gas 118 which can be sent to sweetening and a rich oil 119 which can be recycled to the main fractionator column of the FCCU. The stream 110 rich in C3 and C4 hydrocarbons can be introduced into a stabilizer condenser 17, which generally operates at a pressure comprised between 10.5 and 12 barg, preferably between 11 and 11.3 barg, the resulting stream being introduced into a stabilizer receiver and then separated into two stream, LPG stream 120 which can be sent, thanks to a pump 20 to a LPG treating unit, and a liquid stream 121 which is recycled thanks to reflux pump 21 to the stabilizer column 9. The C3 and C4 molar content of stream 110 is advantageously higher than 98 mol %.

Examples of temperature, pressure and flow rates are given for a particular embodiment in the following table:

| Flow | Temperature (° C.) | Pressure (barg) | Flow rate (kmol/h) |
| --- | --- | --- | --- |
| 101 | 40 | 1.4 | 1778 |
| 101 after 2 | 40 | 13.2 | 4480 |
| 102 | 40 | 13.1 | 3457 |
| 102 after 4 | 40 | 20 | 3457 |
| 102 after 5 | 60 | 19.5 | 3457 |
| 103 | 40 | 13.1 | 1023 |
| 104 | 62 | 14.9 | 833 |
| 105 | 98 | 15.3 | 2624 |
| 105 after 7 | 92 | 11.6 | 2624 |
| 105 after 8 | 109 | 11.4 | 2624 |
| 106 | 140 | 11.5 | 300 |
| 106 after 7 | 93 | 11.3 | 300 |

-continued

| Flow | Temperature (° C.) | Pressure (barg) | Flow rate (kmol/h) |
|---|---|---|---|
| 106 after 10 | 40 | 11 | 300 |
| 106 after 11 | 40 | 13.1 | 300 |
| 106 after 12 | 30 | 12.9 | 300 |
| 107 | 183 | 11.6 | 1018 |
| 107 after 8 | 110 | 11.4 | 1018 |
| 107 after 5 | 64 | 11.2 | 1018 |
| 107 after 23 | 40 | 11 | 1018 |
| 108 | 40 | 11 | 695 |
| 109 | 40 | 11 | 323 |
| 109 after 24 | 40 | 13.5 | 323 |
| 110 | 59 | 11.2 | 3130 |
| 110 after 17 | 55 | 11.1 | 3130 |
| 110 after 18 | 40 | 10.9 | 3130 |
| 110 after 19 | 40 | 10.9 | 3130 |
| 111 | 55.5 | 13.4 | 519 |
| 111 after 14 | 40 | 13.2 | 519 |
| 112 | 54.4 | 13.8 | 1529 |
| 113 | 21 | 22.4 | 575 |
| 114 | 29 | 22.2 | 575 |
| 115 | 38 | 13.2 | 364 |
| 116 | 43 | 12.9 | 455 |
| 117 | 40 | 12.9 | 85 |
| 118 | 51.6 | 12.7 | 405 |
| 119 | 60 | 12.9 | 135 |
| 120 | 40 | 10.9 | 1304 |
| 121 | 40 | 11.3 | 1825 |
| 122 | 38 | 32.5 | 23 |

Results of the method according to the invention are detailed in the following table.

| Propylene absorber operating parameters | | |
|---|---|---|
| Pressure (top) | Hg/cm2g | 12.9 |
| Temperature (Top/Bot) | ° C. | 43/38 |
| Absorbent inlet temperature | ° C. | 30 |
| Gas inlet temperature | ° C. | 40 |

| | | Conventional scheme | Invention |
|---|---|---|---|
| Propylene potential from FCCU | Kmol/h | 591.03 | 591.03 |
| Total propylene loss | kmol/h | 33.42 | 16.97 |
| % overall propylene recovery | % | 94.35 | 97.13 |
| Propylene product flow rate (99.8% pure) | Kg/h | 23493 | 24206 |

The provision of a propylene absorber greatly increases the propylene recovery by more than 2.5% with a low investment.

The method and installation according to the invention are particularly efficient and easy to operate, allowing an upgrade of existing installation and/or conception of very profitable new installations.

The invention claimed is:

1. A method for treating a cracked stream from a fluid catalytic cracker unit (FCCU) comprising the following steps:
    compressing and partly condensing a gas stream from a main fractionator column overhead receiver of the FCCU to produce a compressed and partially condensed gas stream;
    separating the compressed and partially condensed gas stream to produce an upstream liquid and an upstream gas;
    heating the upstream liquid;
    introducing the heated liquid into an upstream stripper to produce a first top stream rich in C2 compounds and a first bottom liquid stream rich in C3+ hydrocarbons;
    introducing the first bottom liquid stream into a first heat exchanger and then into a second heat exchanger to produce a heated first side liquid stream;
    introducing the heated first side liquid stream into a stabilizer column to produce a second top stream rich in C3 and C4 hydrocarbons, a side liquid stream rich in C5 and C6 hydrocarbons, and a stabilizer bottom liquid stream rich in C5, C6 and C7+ hydrocarbons;
    introducing the side liquid stream into the first heat exchanger to produce a cooled side liquid stream;
    further cooling the cooled side liquid stream to produce a further cooled side liquid stream;
    introducing the upstream gas and at least a portion of the stabilizer bottom liquid stream into a primary absorber to produce a third top gas stream and a second bottom liquid stream;
    cooling the third top gas stream;
    introducing the cooled third top gas stream and the further cooled side liquid stream into a propylene absorber;
    recovering a third bottom stream liquid rich in C3 hydrocarbons and a fourth top gas stream poor in C3 hydrocarbons from the propylene absorber; and
    introducing lean oil from the FCCU main fractionator column and the fourth top gas stream into a sponge absorber to recover a fuel gas and a rich oil.

2. The method according to claim 1, further comprising mixing the third bottom liquid stream from the propylene absorber with the compressed and partially condensed stream from the main fractionator column before separating the compressed and partially condensed stream into the upstream liquid and the upstream gas.

3. The method according to claim 1, further comprising introducing the cooled side liquid stream recovered from the first heat exchanger into a third heat exchanger before further cooling the cooled side liquid stream.

4. The method according to claim 3, further comprising introducing the further cooled side liquid stream recovered from the third heat exchanger into fourth heat exchanger before cooling the further cooled side liquid stream.

5. The method according to claim 1, further comprising:
    introducing the second top stream into a condenser;
    retrieving a condensed stream from the condenser;
    cooling the condensed stream to produce a cooled condensed stream; and
    separating the cooled condensed stream into a fourth liquid stream which is introduced into the stabilizer column and a fifth liquid stream which is sent to a LPG treating unit to recover LPG.

6. The method according to claim 1, wherein the first top stream is mixed with the compressed and partially condensed stream from the main fractionator column overhead receiver before the separation of the resulting stream into the upstream liquid and the upstream gas.

7. The method according to claim 1, wherein the second bottom liquid stream is mixed with the compressed and partially condensed stream from the main fractionator column overhead receiver before the separation of the resulting stream into the upstream liquid and the upstream gas.

8. The method according to claim 1, wherein the third bottom liquid stream from the propylene absorber is mixed with the compressed and partially condensed stream from the main fractionator column overhead receiver before the separation of the resulting stream into the upstream liquid and the upstream gas.

9. The method according to claim 1, wherein a gas stream from a propylene recovery unit which is rich in propylene is mixed with the compressed and partially condensed stream from the main fractionator column overhead receiver before the separation of the resulting stream into the upstream liquid and the upstream gas.

\* \* \* \* \*